(12) United States Patent
Taub et al.

(10) Patent No.: US 9,427,916 B2
(45) Date of Patent: Aug. 30, 2016

(54) METHOD FOR PREPARING A PHYSICAL PLASTER MODEL

(75) Inventors: Eldad Taub, Reut (IL); Avi Kopelman, Tenafly, NJ (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 13/082,652

(22) Filed: Apr. 8, 2011

(65) Prior Publication Data
US 2011/0183294 A1 Jul. 28, 2011

Related U.S. Application Data

(63) Continuation of application No. 11/633,417, filed on Dec. 5, 2006, now Pat. No. 7,942,671, which is a continuation of application No. 10/676,257, filed on Oct. 2, 2003, now Pat. No. 7,220,124.

(60) Provisional application No. 60/415,931, filed on Oct. 3, 2002, provisional application No. 60/422,782, filed on Oct. 31, 2002.

(51) Int. Cl.
*A61C 5/00* (2006.01)
*B29C 67/00* (2006.01)
*A61C 11/00* (2006.01)
(Continued)

(52) U.S. Cl.
CPC ......... *B29C 67/0051* (2013.01); *A61C 11/001* (2013.01); *A61C 11/02* (2013.01); *A61C 13/0004* (2013.01); *G06F 17/50* (2013.01); *G06T 17/00* (2013.01); *A61C 9/0046* (2013.01); *A61C 11/08* (2013.01)

(58) Field of Classification Search
CPC ..... A61C 11/02; A61C 11/06; A61C 11/022; A61C 11/08; A61C 11/084; A61C 11/00; A61C 11/001; A61C 9/002
USPC ................ 433/53–67, 74, 213; 434/263–264
See application file for complete search history.

(56) References Cited

U.S. PATENT DOCUMENTS 2,138,254 A 11/1938 Mink
2,333,795 A * 11/1943 Kellerman ............. A61C 19/10
434/264

(Continued)

FOREIGN PATENT DOCUMENTS

AU 3031677 A 5/1979
AU 517102 B2 7/1981
(Continued)

OTHER PUBLICATIONS

European search report and opinion dated Oct. 1, 2012 for EP Application No. 12159572.2.
(Continued)

*Primary Examiner* — Matthew Nelson
(74) *Attorney, Agent, or Firm* — Wilson, Sonsini, Goodrich & Rosati

(57) ABSTRACT

Provided is a method for creating a physical teeth model. Further, the method includes providing a virtual three dimensional (3D) representation of a patient's dentition that includes at least a region of the teeth that includes a tooth stump on which a crown is to be fitted or a region on to which a bridge is to be fitted; and preparing a physical model of the jaws of a subject from a blank, based on information from said virtual 3D image.

21 Claims, 3 Drawing Sheets

(51) Int. Cl.
*A61C 11/02* (2006.01)
*A61C 13/00* (2006.01)
*G06F 17/50* (2006.01)
*G06T 17/00* (2006.01)
*A61C 11/08* (2006.01)
*A61C 9/00* (2006.01)

(56) References Cited

U.S. PATENT DOCUMENTS

| | | |
|---|---|---|
| 2,467,432 A | 4/1949 | Kesling |
| 2,621,406 A | 12/1952 | McPhee |
| 3,407,500 A | 10/1968 | Kesling |
| 3,576,075 A * | 4/1971 | Scott ............... A61C 9/00 264/225 |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,965,576 A * | 6/1976 | Eveland ............ A61C 11/001 433/214 |
| 3,983,628 A | 10/1976 | Acevedo |
| 4,014,096 A | 3/1977 | Dellinger |
| 4,184,255 A * | 1/1980 | Gordon ............ A61C 11/001 433/49 |
| 4,195,046 A | 3/1980 | Kesling |
| 4,253,828 A | 3/1981 | Coles et al. |
| 4,273,533 A * | 6/1981 | Della Croce ........ A61C 11/001 433/213 |
| 4,279,595 A * | 7/1981 | Della Croce ........ A61C 11/00 433/213 |
| 4,315,740 A | 2/1982 | Mercer et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,521,188 A | 6/1985 | Metzler |
| 4,526,540 A | 7/1985 | Dellinger |
| 4,573,917 A | 3/1986 | Erickson |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,812,127 A * | 3/1989 | Hernandez .......... G09B 23/283 132/309 |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,160,262 A * | 11/1992 | Alpern ............ A61C 11/001 433/57 |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A * | 1/1995 | Stern ............ A61C 13/0004 433/213 |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A * | 8/1996 | Stern ............ A61C 13/0004 433/213 |
| 5,562,448 A | 10/1996 | Mushabac |
| 5,569,033 A * | 10/1996 | Michael ............ A61C 9/002 433/213 |
| 5,573,397 A * | 11/1996 | Silva ............ A61C 11/001 433/54 |
| 5,587,912 A | 12/1996 | Andersson et al. |
| 5,605,459 A | 2/1997 | Kuroda et al. |
| 5,607,305 A | 3/1997 | Andersson et al. |
| 5,611,686 A * | 3/1997 | Silva ............ A61C 11/08 433/60 |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,521 A * | 12/1997 | Leasure-Nelson ...... A61F 5/566 128/848 |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,788,489 A * | 8/1998 | Huffman ............ A61C 11/08 433/60 |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |

(56) References Cited

U.S. PATENT DOCUMENTS

| | | |
|---|---|---|
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,431,871 B1 | 8/2002 | Luthardt |
| 6,482,298 B1 | 11/2002 | Bhatnagar |
| 6,497,574 B1 * | 12/2002 | Miller ............... A61C 7/00 433/213 |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,220,124 B2 * | 5/2007 | Taub ............... A61C 11/001 433/213 |
| 7,942,671 B2 * | 5/2011 | Taub ............... A61C 11/001 433/213 |
| 8,845,330 B2 | 9/2014 | Taub et al. |
| 2001/0002310 A1 * | 5/2001 | Chishti ............... A61C 7/00 433/24 |
| 2002/0006597 A1 | 1/2002 | Andreiko et al. |
| 2002/0013636 A1 | 1/2002 | O'Brien et al. |
| 2002/0015934 A1 | 2/2002 | Rubbert et al. |
| 2002/0048741 A1 * | 4/2002 | Jordan ............... A61C 13/0004 433/73 |
| 2002/0064759 A1 | 5/2002 | Durbin et al. |
| 2002/0081554 A1 | 6/2002 | Marshall et al. |
| 2002/0094503 A1 * | 7/2002 | Chishti ............... A61C 7/08 433/34 |
| 2002/0102514 A1 * | 8/2002 | Huffman ............... A61C 9/002 433/34 |
| 2002/0110786 A1 * | 8/2002 | Dillier ............... A61C 13/0004 433/213 |
| 2002/0150859 A1 | 10/2002 | Imgrund et al. |
| 2002/0164556 A1 | 11/2002 | Huffman |
| 2003/0009252 A1 | 1/2003 | Pavlovskaia et al. |
| 2003/0012423 A1 | 1/2003 | Boland et al. |
| 2003/0083750 A1 * | 5/2003 | Schulter ............... A61C 8/0006 623/17.18 |
| 2003/0118970 A1 * | 6/2003 | Rusin ............... A61C 13/0027 433/213 |
| 2003/0124492 A1 * | 7/2003 | Perot ............... A61C 9/002 433/213 |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2004/0172150 A1 | 9/2004 | Perot et al. |
| 2004/0197740 A1 | 10/2004 | Amar |
| 2005/0055118 A1 | 3/2005 | Nikolskiy et al. |
| 2007/0154867 A1 | 7/2007 | Taub et al. |
| 2014/0336809 A1 | 11/2014 | Taub et al. |

FOREIGN PATENT DOCUMENTS

| | | |
|---|---|---|
| AU | 5598894 A | 6/1994 |
| CA | 1121955 | 4/1982 |
| DE | 395385 C | 5/1924 |
| DE | 2749802 | 5/1978 |
| DE | 35 41 891 A1 | 6/1987 |
| DE | 29705816 U1 * | 5/1997 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | 97/03622 A1 | 2/1997 |
| WO | WO 98/32394 A1 | 7/1998 |
| WO | WO 98/44865 A1 | 10/1998 |
| WO | 98/52493 A1 | 11/1998 |
| WO | WO 98/58596 A1 | 12/1998 |
| WO | WO 99/15100 A1 | 4/1999 |
| WO | 00/08415 A1 | 2/2000 |
| WO | 00/25677 A1 | 5/2000 |

OTHER PUBLICATIONS

AADR. American Association for Dental Research, Summary of Activities, Mar. 20-23,1980, Los Angeles, CA, p. 195.

Alcaniz, et al, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures, " AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO

(56) References Cited

OTHER PUBLICATIONS

Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill, Aug. 26-30, 1975, pp. 142-166.

Baumrind, "Integrated Three-Dimensional Craniofacial Mapping: Background, Principles, and Perspectives," Semin in Orthod., 7(4):223-232 (Dec. 2001).

Begole et al., "A Computer System for the Analysis of Dental Casts," The Angle Orthod., 51(3):253-259 (Jul. 1981).

Bernard et al.," Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/-pbourke/prolection/coords>.

Boyd et al., "Three Dimensional Diagnosis and Orthodontic Treatment of Complex Malocclusions With the Invisalipn Appliance," Semin Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Burstone et al., Precision Adjustment of the Transpalatal Lingual Arch: Computer Arch Form in Predetermination, Am, Journal of Orthodontics, vol. 79, No. 2 (Feb. 1981), pp. 115-133.

Cardinal Industrial Finishes, Powder Coatings information posted at <http://www.cardinalpaint.com> on Aug. 25, 2000, 2 pages.

Carnaghan, "An Alternative to Holograms for the Portrayal of Human Teeth," 4th Intl. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production, pp. 1-7 (Jan. 1992).

Definition for gingiva. Dictionary.com p. 1-3. Retrieved from the internet Nov. 5, 2004 <http://reference.com/search/search?q=gingiva>.

Defranco et al., "Three-Dimensional Large Displacement Analysis of Orthodontic Appliances," J. Biomechanics, 9:793-801 (1976).

Dental Institute University of Zurich Switzerland, Program for International Symposium on Computer Restorations: State of the Art of the CEREC—Method, May 1991, 2 pages total.

Dentrac Corporation, Dentrac document, pp. 4-13 (1992).

DENT-X posted on Sep. 24, 1998 at <http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances—Pro Lab, 1 page (1997).

Duret et al, "CAD-CAM in Dentistry," J. Am. Dent. Assoc. 117:715-720 (Nov. 1988).

Duret et al., "CAD/CAM Imaging in Dentistry," Curr. Opin. Dent., 1:150-154 (1991).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et al., "Automated Finite Element Modeling of a Human Mandible with Dental Implants," WSCG '98—Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

GIM-ALLDENT Deutschland, "Das DUX System: Die Technik," 2 pages total (2002).

Gottleib et al., "JCO Interviews Dr. James A. McNamara, Jr., on the Frankel Appliance: Part 2: Clinical 1-1 Management,"J. Clin. Orthod., 16(6):390-407 (Jun. 1982).

Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

(56) References Cited

OTHER PUBLICATIONS

Heaven et al., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulating-stressputonfa...>.

Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 p. 1998).

JCO Interviews, Craig Andreiko, DDS, on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, Am. J. Orthod. Oral Surg. (1946) 32:285-293.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus:Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

Procera Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <http://www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

(56) References Cited

OTHER PUBLICATIONS

Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information—Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).

Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); I11.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); I11. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

* cited by examiner

METHOD FOR PREPARING A PHYSICAL PLASTER MODEL

This application is a Continuation application filed under 35 U.S.C. §120 of U.S. patent application Ser. No. 11/633,417, filed on Dec. 5, 2006, which was a Continuation application filed under 35 U.S.C. §120 of U.S. patent application Ser. No. 10/676,257, filed on Oct. 2, 2003, now U.S. Pat. No. 7,220,124, which was an application claiming the benefit under 35 U.S.C. §119(e) of U.S. Provisional Application No. 60/415,931, filed on Oct. 3, 2002, and which was an application claiming the benefit under 35 U.S.C. §119(e) of U.S. Provisional Application No. 60/422,782, filed on Oct. 31, 2002, the content of each of which is hereby incorporated by reference in its entirety.

FIELD OF THE INVENTION

This invention relates to the field of dentistry and in particular to a method of preparing plaster models for use in orthodontics, prosthodontics and other aspects of dental medicine.

BACKGROUND OF THE INVENTION

For a dentist or a dental technician, one of the main difficulties in making a working physical model of the teeth, including the inter-occlusal relationship between the jaws (also known by the term "master cast" or "working cast"), lies in respecting the position of a patient's artificial jaws when the teeth are in Centric Occlusion position. Separate molding of the upper and the lower teeth followed by the manual articulation of the two parts is a constant source of error. The precision of the cast depends on several factors, including, inter alia, the accuracy of the impressions and wax bites, the material from which the cast is constructed, and the identification of the anatomic. In addition, traditional methods using pins do not prevent linear expansion of the cast. This can result in the deformation of the new teeth that do not correspond perfectly to the original. Thus, the more precisely the working cast reproduces the anatomy of the mouth, the more accurate will be the spatial position, and the static and dynamic relationships. This provides a better possibility of producing a biomechanically acceptable restoration.

In order to reproduce with high precision the mechanical equivalent of functional and non-functional movements within the mouth, articulators (also known by the term "occluding devices") have been and still are under development. The articulators are used to precisely hold models of a patient's upper and lower teeth, so a dentist can study their bite or make a restoration.

Articulators are primarily used when a crown needs to be prepared. According to current practice, after diagnosing in a patient the need for a crown or a bridge, the dentist cuts the tooth to be reconstructed by the crown or bridge and prepares two impressions and a wax bite of the patient's jaws. One impression is of the area prepared for the crown and the surrounding area. The other impression is of the opposite jaw. A wax bite is used to record the spatial relation between the jaws at occlusion. Based on the impressions, wax bite and written instructions of the dentist, a technician prepares in a lab the corresponding plaster jaws which are trimmed and mounted on an articulator. Using the wax bites, the spatial relation between the jaws is determined. At this stage, the tooth within the preparation to be reconstructed is temporarily separated from the plaster so that the area with the anatomic information (the area defining the anatomic contour) and the finish line are exposed. The finish line is typically marked manually by the lab technician in ink on the preparation and a crown is built based on the resulting preparation. The quality of the crown prepared is examined by placing the crown on the preparation in the articulator and verifying that there is a good occlusion of the crown with the opposite teeth. If in the affirmative, the crown is sent to the dentist for placement on the preparation in the patient's mouth.

SUMMARY OF THE INVENTION

The present invention concerns a unique method of preparing a physical working teeth model of teeth, e.g. a model made of hard plaster, used for the fabrication of orthodontics and prosthodontics Crown or Bridges. The method utilizes a three dimensional (3D) virtual image of the patient's dentition or parts of it. Based on digital data representing said 3D image, a physical 3D teeth model is constructed.

The term "teeth model" will be used to denote a physical, three-dimensional representation of teeth in a solid matrix having a surface relief corresponding to the teeth arrangement of the individual. Such a model may be a "positive teeth model", comprising a teeth replica, namely, a model where each tooth is represented by a projection or bulge having contours identical in size and shape to the corresponding tooth; or a "negative teeth model", where each tooth is represented by a cavity or recess with contours identical in size, but opposite in shape to the contours of the corresponding tooth.

Thus, according to one embodiment, the invention provides a method for preparing a physical positive working model of a patient's dentition. According to another embodiment, the invention provides a method for preparing a physical negative model from which a positive working model can be fabricated, according to known dentistry procedures.

The method of the invention is of particular use in the construction of crowns or bridges. Thus, according to the invention, the 3D virtual image comprises at least the region of the teeth that includes a tooth stump on which a crown is to be fitted or a region on to which a bridge is to be fitted. Based on the virtual image of the dentition, a physical model of the two jaws is prepared. Thereafter, the resulting model, being positive or negative, as the case may be, is used for a variety of purposes, for example to prepare a crown, a bridge or other dental appliance; to analyze the relationship between the upper and lower jaws; to show the patient the crown or bridge; etc.

Alternatively, the virtual image may be further manipulated and based on the digital data representing the image, a virtual crown or bridge is constructed. Based on the virtual image of the crown or bridge, a physical model of the crown or bridge is prepared.

A virtual three-dimensional (3D) image is obtained e.g. in the manner as described in PCT publication No. WO97/03622 or PCT publication No. WO00/08415.

The dentist (or the technician, as the case may be) may construct a virtual image of the patient's dentition either with or without the virtual image of the crown or bridge, and then may send such data to the lab technician. There, a physical model may be prepared, e.g. by milling, 3D lithography or by any other appropriate means, according to said data. The physical model prepared by the technician can be sent to the dentist, for his approval (the physical model can also be fabricated at the dentist's office).

The physical model has typically one member that represents the upper jaw and another that represents the lower jaw. It order to render it easy to match these two members to one another, they may be produced with markings or appropriate physical alignment arrangement for aligning the jaws to represent the alignment of the jaws of the patient. Said data that includes the virtual image thus preferably includes also data bits for producing such markings or arrangement.

Markings may be in the form of depressions or protrusions on the face of the members that are made such so as to provide the technician with a tool for the proper alignment of the two members. A physical alignment arrangement may include a mounting arrangement for mounting the two members to an articulator to yield a proper occlusion alignment. By another example, the physical alignment arrangement may include one or more alignment reference components in one member that once fitted with one or more corresponding components in the other member, ensure proper alignment of the two members.

Thus, the present invention provides a dental articulator that precisely simulates the occlusion relationship of the jaws as well as the three-dimensional movement of a human jaw.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

As is true in any method of making a physical model, e.g. a plaster model of a patient's dentition, it is most important to start with an accurate representation of the jaws and teeth and the inter-occlusal relationship between the jaws. For this purpose, the instant invention relies on a virtual model of the patient's dentition.

Digital data representing a virtual teeth model may be obtained by a variety of methods, such as that described in PCT Application No. PCT/IL96/00036 (publication No. WO97/03622) and in PCT Application No. PCT/IL99/00431 (publication No. WO00/08415). The virtual three-dimensional image may be manipulated, for example, in a manner described in PCT Application No. PCT/IL99/00577 (publication No. WO00/25677). In particular, the virtual three-dimensional (3D) image is obtained by utilizing a physical negative teeth model, e.g. a negative teeth model that comprises the teeth impression by means of an impression matrix. The physical negative teeth model may be used as such, thus providing digital negative representation of the patient's dentition, from which a digital positive representation of the patient's dentition may be digitally obtained. Alternatively, the physical negative teeth model may be used to prepare a physical positive teeth model, from which a digital positive teeth representation is provided.

After the virtual image is generated, the display is typically a computerized display, provided with software permitting the technician to visualize the virtual image from different angles. As will be appreciated, the invention is not limited to any specific display means and any means for presenting the image such as, for example, in a printed format, on a computer display screen, etc., may be employed in accordance with the invention.

In most situations, the dentist will take three virtual impressions. One impression is of the preparation area for the crown, bridge or other dental appliances, along with the surrounding teeth. Another impression is of the teeth on the opposite jaw. The third impression records the spatial relationship between and the spacing of the two jaws in a centric occlusion. This information from the virtual impressions is placed in a 3D file that contains the two jaws and the spatial relationship between them in occlusion. Thereafter, the 3D file may be transferred to the laboratory.

Figure 1:
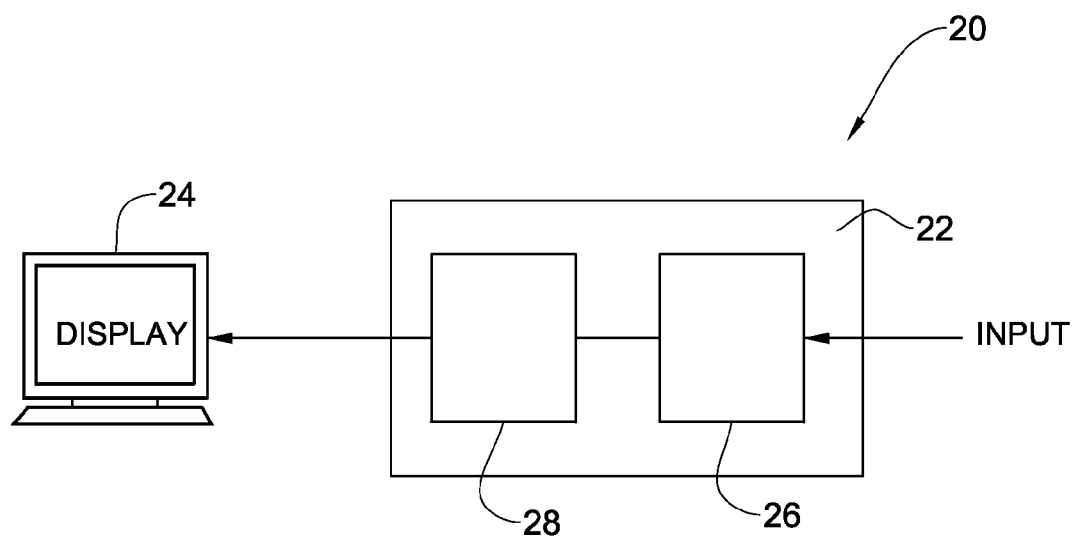
FIG. 1 shows, by way of a block diagram, a computerized device for constructing a virtual impression of the patient's dentition.

Reference is made to FIG. 1 showing a computerized device generally designated 20 including a processor 22 and a display unit 24. Running in the processor 22 is a first software utility 26 that receives an input of a three dimensional virtual teeth model and then processes, automatically or through the user, manipulable software utility 28, to construct a three dimensional virtual teeth model that includes the region that is to be treated, which can then be fed for display to display unit 24. By this means, the virtual impression of the dentition is made and the information may then be stored. The technician may then simulate any treatment area on the computer. For example, the cutout in the tooth for the crown can be simulated, along with fitting of the crown.

Figure 2:
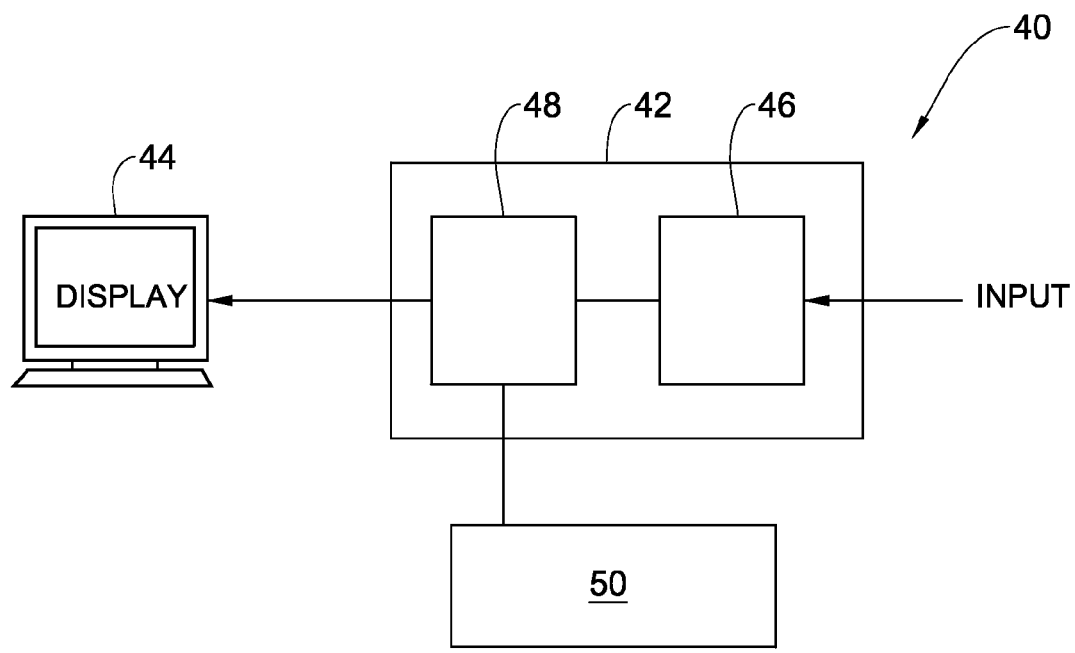
FIG. 2 shows, by way of a block diagram, a computerized device for milling a plaster model, based on the information from the virtual impression, in accordance with an embodiment of the invention.

Reference is now being made to FIG. 2 showing a system generally designated 40. In FIG. 2, like components to those shown in FIG. 1, are given the same reference numerals shifted by 20 (namely component 42, for example, is functionally identical to component 22 in FIG. 1). System 40 of FIG. 2 includes an apparatus 50 that is used to construct a physical model utilizing digital data received from software utility 48. For this purpose, a Computer Numerical Control (CNC) milling machine 50 may be used. However, the invention is not limited to the use of a CNC machine and any other CAM (Computer Aided Manufacturing) technology that can produce a physical model out of virtual data may be used.

To manufacture a crown, a bridge, or any dental appliance, the lab technician requires two physical jaws models mounted on an articulator or placed in the correct spatial orientation one against the other. According to this method, the information for the two jaws and their spatial relationship in occlusion is in a digital 3D file. Alternatively, or in addition, the proper occlusion may be determined in a manner disclosed in WO 98/52493. The computer guided milling (or other technology) machine is connected to the computer with the 3D file of the virtual impression, and then a physical model of each one of the jaws is milled from a blank made of plaster, or other appropriate material taking into consideration also the spatial relation between the two jaws and their occlusion. At this point, the technician has his necessary physical model and can proceed with making the crown or the bridge.

Based on information from the virtual 3D image, the dentist or a technician may generate a 3D model of a crown to be fitted on a tooth stump or of a bridge to be fitted on the tooth surface, to generate a digital file on which basis the lab technician, through the use of a computer driven milling machine, may generate a physical crown, bridge or other dental appliances.

Figure 3:
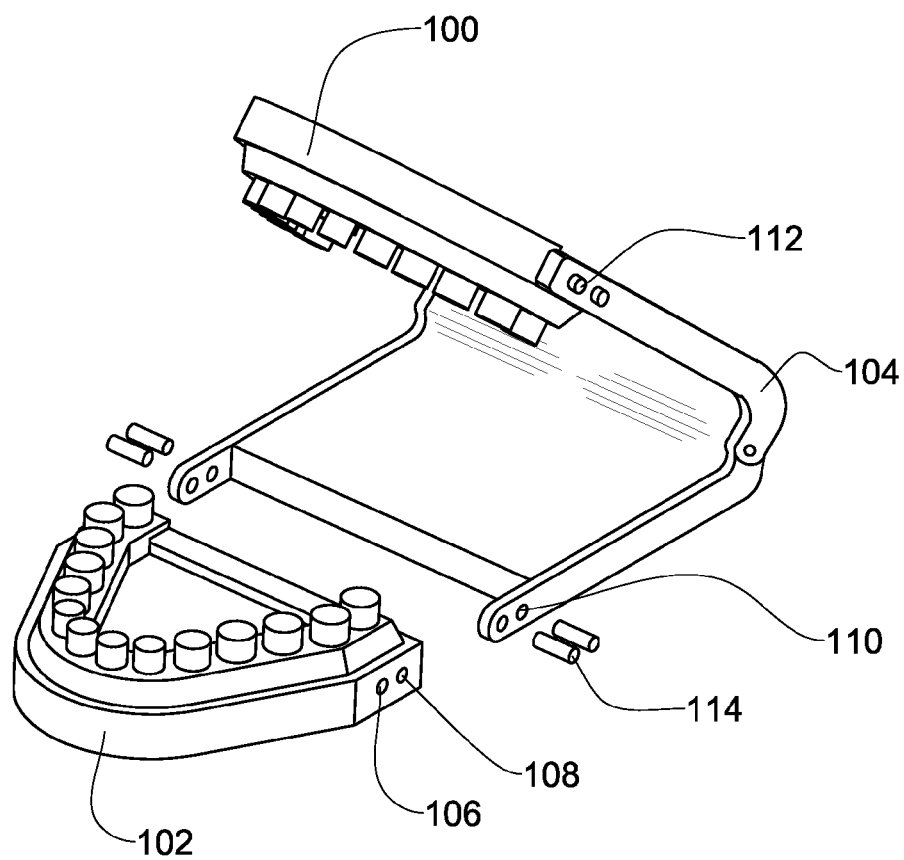
FIG. 3 shows a perspective view of the plaster model arranged on an articulator.

It should be noted that the physical model generated by device 40 might be a positive model or alternatively, a negative model. FIG. 3 shows plaster cast members 100 and 102 fabricated according to the invention and representing the upper and lower jaws, respectively. The members 100 and 102 can be mounted on an articulator 104 to simulate the proper occlusion relation. For that both members have articulator engagement portions 106 with reference holes 108 that can be registered with holes 110 engagement bit 112 of articulator 104, which engagement is through pins 114. The engagement portion 106 with the reference holes 108, are initially defined in the virtual 3D image. In this model the proper inter-jaw occlusion are first defined, as explained above, and after the proper inter-jaw occlusion is determined, the virtual 3D model may be virtually combined with an articulator to define the articulator-engagement portion with its reference holes. This is then included in the digital file used to produce the plaster model. The reference holes may be produced automatically by the milling machine. However, the reference holes may be difficult to produce by the milling machine and may need to be produced after milling, as a separate step, for example, based on markings produced automatically during the milling procedure.

Figure 4:
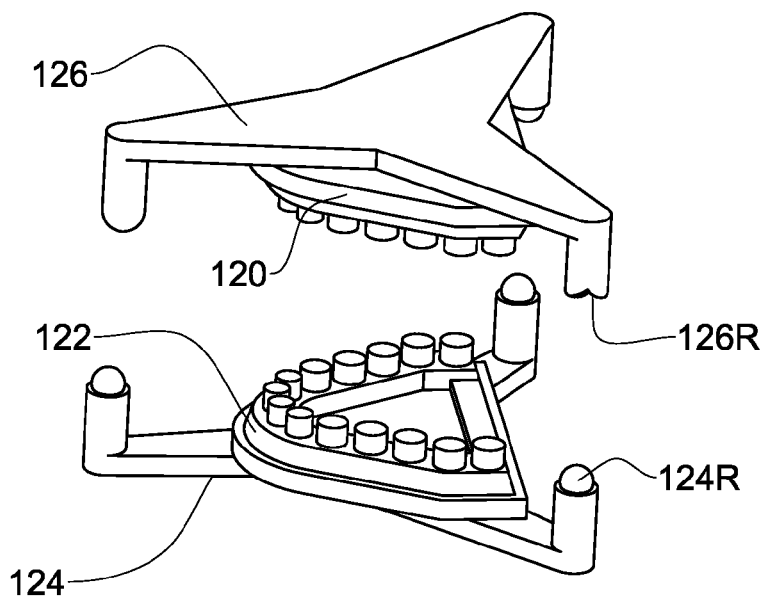
FIG. 4 shows a perspective view of the plaster model with references for aligning the jaws.

Reference is now made to FIG. 4 that shows another embodiment of a manner for proper alignment of the two cast members. The two cast members 120 and 122 are produced each with a corresponding aligning structures 124 and 126. Each of these aligning structures includes positioning reference components 124R and 126R, respectively, the former having an end abutment, that fits into a matching recess in the latter. This alignment structure is first produced virtually after virtual alignment of the two jaw members and thereafter structures 124 and 126 may then be added. The data file prepared from the virtual model and that is utilized for manufacture of the physical members 120 and 122, this includes, according to this embodiment, also data for integral production of said structures.

As may be appreciated, the lab technician has to build a crown, a bridge, or other dental appliances, that will have a good fit on the prepared area of the tooth. Contact with the surrounding teeth must be good, and such as in the case of crowns, there must also be correct contact with teeth on the opposing jaw. If the crown does not fit correctly, the bite will be affected and the crown will not fit comfortably in the mouth. The articulator is used to mount the model, so the crown and be formed and properly fitted. This is why the model must be highly accurate, or the crown will not fit correctly in the patient's mouth. It is from this information that an accurate 3D file of the dentition is created, and the milling of the plaster physical mold is based on the information in this 3D file. Due to the enhanced accuracy of the information about the dentition, the physical model can be made more accurately, thereby leading to a more accurate manufacture of the crown.

Figure 5:
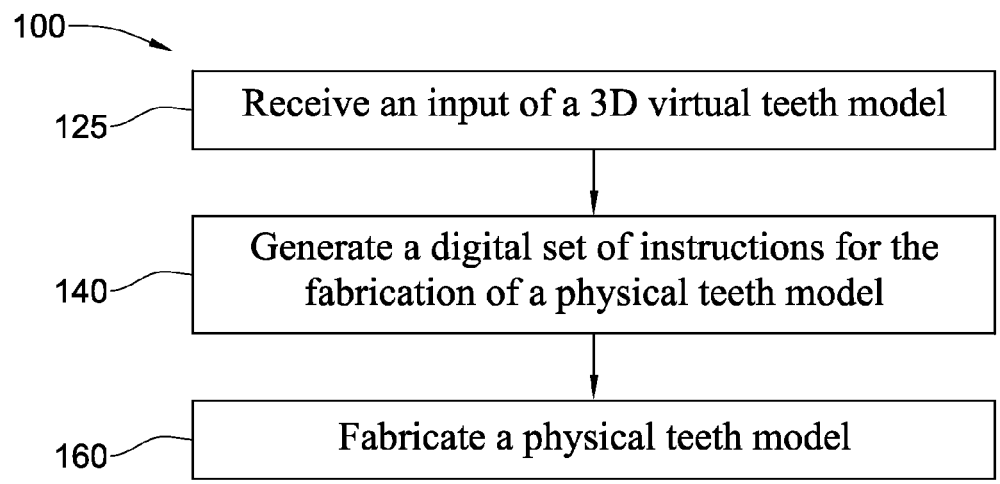
FIG. 5 shows, by way of a flow chart, a method for fabricating a physical teeth model, in accordance with an embodiment of the invention.

Reference is now being made to FIG. 5, and the reader is referred to FIG. 2 for a complete understanding of their function. Illustrated in FIG. 5 are the main steps 100 in a method of the invention for the fabrication of a physical teeth model utilizing the device 40 and a CAM machine (CNC milling machine 50, in this example) connectable to the device 40, as shown in FIG. 2.

At step 125, the device 40 receives an input of a 3D virtual teeth model (constituting a 3D representation of a patient's dentition), and based on which, generates, at 140, digital information for the fabrication of a physical teeth model. Then at step 160, the machine 50 fabricates the physical teeth model.

It should be noted that additional steps might be needed and carried out manually or automatically, e.g., for the generation of additional digital information, which can be displayed by the display utility 24, as previously explained. It should also be noted that the machine 50 does not need to be part of the device 40 and can be a separate utility. In the later case, the digital information generated by the device 40 is transmitted to the machine 50 via a direct connection (through wires or wireless communication means) or via a communication network (e.g. the Internet).

According to the common CAD techniques, soft materials such as wax may be used for the fabrication of the physical model. However, the fabricated physical model made of such relative soft materials is easily deformable by mechanical stresses. This outcome is highly undesirable in the context of dentistry, in which a positive working model is used, for example for the creation of orthodontic or prosthodontics appliances. Any deformation in the fabricated positive model degrades the precision of the appliance based on the positive model, as well as degrades the quality of the orthodontics and prosthodontics treatment.

The present invention, by one of its embodiment, solves the above problem by providing a method for the fabrication of a precise negative model, from which a positive working model can then be produced, for example from a hard plaster, by utilizing traditional dentistry procedures.

Figure 6:
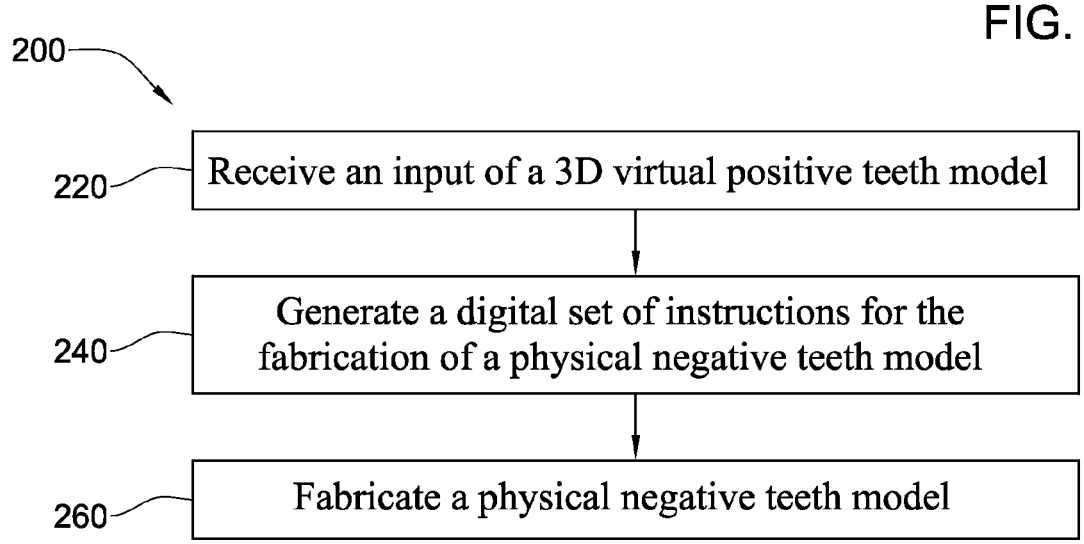
FIG. 6 and FIG. 7 illustrate two specific examples, respectively, of the method of FIG. 5.
Figure 7:
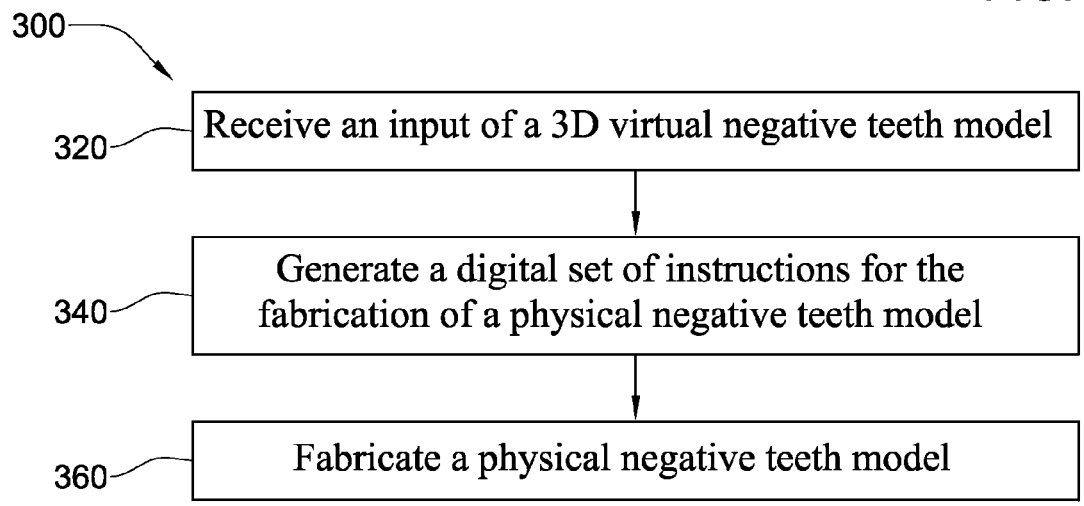

FIG. 6 and FIG. 7 more specifically illustrate flow diagrams 200 and 300 (respectively) for the fabrication of a negative teeth model utilizing the method of FIG. 5. In the example of FIG. 6, the device 40 receives an input of a 3D virtual positive teeth model (step 220), and generates digital information for the fabrication of a physical negative teeth model (step 240). The machine 50, being a part of or connectable to the device 40, operates to fabricate the physical negative teeth model (step 260). At a later stage (not shown), the fabricated physical negative teeth model is used for the fabrication of a positive working model, according to known procedures, e.g. by filling the negative cast with a hard plaster and removing the negative cast.

In the example of FIG. 7, the device 40 receives an input of a 3D virtual negative teeth model (step 320). The processing of this data for the generation of the digital information for the fabrication of the physical negative teeth model (at step 340) might not need the generation of a digital positive model. However, an additional step (not shown) can be carried out between steps 320 and 340, in which a digital positive model, from which the information is derived, is generated.

As mentioned above, the fabricated physical model can bear marking or articulator engagement portions, for proper relations. When a negative model is fabricated, it bears a negative marking and/or engagement portions (e.g. depressions), thus providing the positive working model with positive marking and/or engagement portions (e.g. corresponding protrusions).

It should be noted that a dedicated device could implement the procedures 100, 200 and 300. Alternatively, these procedures can be integrated with other computerized dentistry methods, e.g. virtual treatment plan and the like.

While some preferred embodiments have been shown and illustrated, it is to be understood by a skilled person that it is not intended thereby to limit the disclosure, but rather it is intended to cover all modifications and arrangements falling within the spirit and scope of the present invention.

The invention claimed is:

1. A system for use in fabricating dental appliances, said system comprising:
   a processor operably coupled to a computer readable storage medium comprising instructions that, when executed, cause the processor to:
      receive a virtual three dimensional (3D) representation of a patient's lower arch, the patient's upper arch, and an occlusion alignment between the upper and lower arches, and
      modify the virtual 3D representation by adding a first virtual alignment structure to the lower arch and a second virtual alignment structure to the upper arch, the first and second virtual alignment structures shaped to engage each other to produce the occlusion alignment between the upper and lower arches; and
   a physical model of the dentition comprising,
      a lower arch model having lower teeth and an upper arch model having upper teeth, said physical model based on the modified virtual 3D representation,
      a first single continuous piece comprising the lower arch model and a first alignment structure extending from and integrally formed with the lower arch model, the first alignment structure shaped according to the first virtual alignment structure, and
      a second single continuous piece comprising the upper arch model and a second alignment structure extending from and integrally formed with the upper arch model, the second alignment structure shaped according to the second virtual alignment structure,
      wherein one or more of a first plurality of first positioning reference components or a second plurality of second positioning reference components are formed to allow the first plurality of first positioning reference components to come into reversible contact with the second plurality of second positioning reference components in a fixed spatial relationship to thereby provide the occlusion alignment between the lower teeth of the lower arch model and the upper teeth of the upper arch model based on said modified virtual 3D representation.

2. The system according to claim 1, wherein said model is a plaster model.

3. The system according to claim 1, wherein said model is a positive teeth model.

4. The system of claim 1, wherein the virtual 3D representation comprises a dental region on which a dental appliance is to be fitted, and wherein the dental appliance is a crown or a bridge, and wherein said dental region includes a tooth stump on which the crown is to be fitted or a region on to which a bridge is to be fitted.

5. The system of claim 1, wherein the virtual 3D representation comprises a dental region on which a dental appliance is to be fitted, and wherein the dental appliance is a crown, and wherein said dental region includes a tooth stump on which the crown is to be fitted.

6. The system of claim 1, wherein the virtual 3D representation comprises a dental region on which a dental appliance is to be fitted, and wherein the dental appliance is a bridge, and wherein said dental region includes a tooth stump on which the bridge is to be fitted.

7. The system of claim 1, wherein the first alignment structure and the second alignment structure are arranged to place the upper teeth in contact with the lower teeth of the physical model upon engagement of the first plurality of first positioning reference components with the second plurality of second positioning reference components.

8. The system of claim 1, wherein the first alignment structure comprises three positioning reference components.

9. The system of claim 1, wherein the second alignment structure comprises three positioning reference components.

10. The system of claim 1, wherein the first plurality of first positioning reference components and the second plurality of second positioning reference components comprise end abutments and matching recesses.

11. A system for use in fabricating dental appliances, the system comprising:
    a processor operably coupled to a computer readable storage medium comprising instructions that, when executed, cause the processor to:
       receive a virtual three dimensional (3D) representation of a patient's lower arch, the patient's upper arch, and an occlusion alignment between the upper and lower arches, and
       modify the virtual 3D representation by adding a first plurality of virtual alignment structures to the lower arch and a second plurality of virtual alignment structures to the upper arch, the first and second pluralities of virtual alignment structures shaped to engage each other to produce the occlusion alignment between the upper and lower arches; and
    a physical model of the dentition comprising,
       a dental region configured to fit a crown or a bridge,
       a first single continuous piece comprising a lower arch and a first plurality of integral alignment structures extending from and integrally formed with the lower arch, the first plurality of integral alignment structures shaped according to the first plurality of virtual alignment structures, and
       a second single continuous piece comprising an upper arch and a second plurality of corresponding integral alignment structures extending from and integrally formed with the upper arch, the second plurality of corresponding integral alignment structures shaped according to the second plurality of virtual alignment structures,
    wherein the first plurality of integral alignment structures comprises a first plurality of positioning reference components and the second plurality of corresponding integral alignment structures comprises a second plurality of positioning reference components to engage the first plurality of positioning reference components, and
    wherein each of the first plurality of positioning reference components is shaped to fit a corresponding second reference component of the second plurality of positioning reference components in order to define the occlusion alignment with the first plurality of integral alignment structures and the second plurality of corresponding integral alignment structures.

12. The system of claim 11, wherein the dental appliance is a crown, and wherein said dental region includes a tooth stump on which the crown is to be fitted.

13. The system of claim 11, wherein the dental appliance is a bridge, and wherein said dental region includes a tooth stump on which the bridge is to be fitted.

14. The system of claim 11, wherein the first plurality of integral alignment structures and the second plurality of integral alignment structures are arranged to place the upper teeth in contact with the lower teeth of the physical model upon engagement of the first plurality of integral alignment structures with the second plurality of integral alignment structures.

15. The system of claim 11, wherein the first plurality of integral alignment structures comprises three positioning reference components.

16. The system of claim 11, wherein the second plurality of corresponding integral alignment structures comprises three positioning reference components.

17. The system of claim 11, wherein the first plurality of positioning reference components and the second plurality of positioning reference components comprise end abutments and matching recesses.

18. A system for use in fabricating dental appliances, the system comprising:
 a processor operably coupled to a computer readable storage medium comprising instructions that, when executed, cause the processor to:
  receive a virtual three dimensional (3D) representation of a patient's lower arch, the patient's upper arch, and an occlusion alignment between the upper and lower arches, and
  modify the virtual 3D representation by adding a first plurality of virtual alignment arms to the lower arch and a second plurality of virtual alignment arms to the upper arch, the first and second pluralities of virtual alignment arms shaped to engage each other to produce the occlusion alignment between the upper and lower arches; and
 a physical teeth model of a patient's dentition, the model comprising,
  a dental region configured to fit a dental appliance;
  a first single continuous piece comprising the lower arch and a first plurality of integral alignment arms extending from and integrally formed with the lower arch, the first plurality of integral alignment arms shaped according to the first plurality of virtual alignment arms, and
  a second single continuous piece comprising the upper arch and a second plurality of corresponding integral alignment arms extending from and integrally formed with the upper arch, the second plurality of corresponding integral alignment arms shaped according to the second plurality of virtual alignment arms,
 wherein the first plurality of integral alignment arms comprises a first plurality of positioning reference components and the second plurality of corresponding integral alignment arms comprises a second plurality of positioning reference components,
 wherein each of the first plurality of positioning reference components is shaped to match a corresponding second positioning reference component of the second plurality of positioning reference components in order to define the occlusion alignment with the first plurality of integral alignment arms and the second plurality of corresponding integral alignment arms extending between the lower teeth of the lower arch and the upper teeth of the upper arch, and
 wherein the first plurality of positioning reference components and the second plurality of positioning reference components comprise end abutments and matching recesses.

19. The system of claim 18, wherein the first plurality of integral alignment arms and the second plurality of corresponding integral alignment arms are arranged to place the upper teeth in contact with the lower teeth of the physical model upon engagement of the first plurality of integral alignment arms with the second plurality of corresponding integral alignment arms.

20. The system of claim 18, wherein the first plurality of integral alignment arms comprises three positioning reference components.

21. The system of claim 18, wherein the second plurality of corresponding integral alignment arms comprises three positioning reference components.

* * * * *